United States Patent
McCaffrey et al.

(10) Patent No.: US 9,913,585 B2
(45) Date of Patent: Mar. 13, 2018

(54) CATHETER FOR PROVIDING VASCULAR PRESSURE MEASUREMENTS

(71) Applicant: Medtronic Vascular Galway, Ballybrit, Galway (IE)

(72) Inventors: Gerry McCaffrey, Ballybrit (IE); Fiachra Sweeney, Ballybrit (IE); Barry O'Connell, Ballybrit (IE); Christopher Murphy, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 526 days.

(21) Appl. No.: 14/155,723

(22) Filed: Jan. 15, 2014

(65) Prior Publication Data

US 2015/0196210 A1 Jul. 16, 2015

(51) Int. Cl.
| | |
|---|---|
| *A61B 5/02* | (2006.01) |
| *A61B 5/0215* | (2006.01) |
| *A61B 5/00* | (2006.01) |
| *A61M 25/09* | (2006.01) |
| *A61M 25/00* | (2006.01) |
| *A61B 5/026* | (2006.01) |
| *A61B 5/021* | (2006.01) |
| *A61M 25/01* | (2006.01) |

(52) U.S. Cl.
CPC .......... *A61B 5/02158* (2013.01); *A61B 5/026* (2013.01); *A61B 5/02007* (2013.01); *A61B 5/02141* (2013.01); *A61B 5/6852* (2013.01); *A61M 25/007* (2013.01); *A61M 25/09* (2013.01); *A61M 2025/0002* (2013.01); *A61M 2025/0004* (2013.01); *A61M 2025/0175* (2013.01); *A61M 2025/0183* (2013.01)

(58) Field of Classification Search
None
See application file for complete search history.

(56) References Cited

U.S. PATENT DOCUMENTS

| | | |
|---|---|---|
| 4,718,425 A | 1/1988 | Tanaka et al. |
| 4,771,782 A | 9/1988 | Millar |
| 4,796,641 A | 1/1989 | Mills et al. |

(Continued)

FOREIGN PATENT DOCUMENTS

| | | |
|---|---|---|
| DE | 102008045878 A1 | 3/2010 |
| EP | 0263190 | 10/1986 |

(Continued)

*Primary Examiner* — Michael R Bloch (57) ABSTRACT

A catheter is disclosed for providing pressure measurements at a vascular lesion. The catheter includes an outer component having a side opening the providing transverse access to a lumen thereof and an inner component slidably disposed within the lumen. The inner component has a guidewire lumen with a proximal side port. When the inner component is longitudinally translated relative to the outer component, the side port of the inner component is accessible through the side opening of the outer component for providing transverse access to a guidewire. A first pressure sensor is disposed proximate of a distal end of the outer component and a second pressure sensor is disposed proximate of a distal end of the inner component, such that relative longitudinal translation between the inner and outer components permits a distance between the first and second pressure sensors to be varied.

20 Claims, 5 Drawing Sheets

(56) References Cited

U.S. PATENT DOCUMENTS

| | | |
|---|---|---|
| 4,815,472 A | 3/1989 | Wise et al. |
| 4,850,358 A | 7/1989 | Millar |
| 4,901,731 A | 2/1990 | Millar |
| 4,924,877 A | 5/1990 | Brooks |
| 4,928,693 A | 5/1990 | Goodin et al. |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A | 7/1991 | Lieber et al. |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A * | 1/1997 | Shoup ............... A61M 25/0075 604/103.1 |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A * | 2/1998 | Corl ..................... A61B 5/0215 600/486 |
| 5,813,997 A | 9/1998 | Imran et al. |
| 5,827,243 A | 10/1998 | Palestrant |
| 5,873,835 A | 2/1999 | Hastings et al. |
| 5,902,248 A | 5/1999 | Millar et al. |
| 5,964,714 A | 10/1999 | Lafontaine |
| 6,033,366 A | 3/2000 | Brockway et al. |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,182,513 B1 | 2/2001 | Stemme et al. |
| 6,193,669 B1 | 2/2001 | Degany et al. |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 11/2001 | Hoek et al. |
| 6,336,906 B1 | 1/2002 | Hammarstrom et al. |
| 6,354,999 B1 | 3/2002 | Dgany et al. |
| 6,379,308 B1 | 4/2002 | Brockway et al. |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B2 | 5/2004 | Atsumi |
| 6,754,608 B2 | 6/2004 | Svanerudh et al. |
| 6,767,327 B1 | 7/2004 | Corl et al. |
| 6,821,287 B1 * | 11/2004 | Jang .................. A61M 25/0023 604/160 |
| 6,860,851 B2 * | 3/2005 | Knudson ............ A61B 5/14503 600/309 |
| 6,868,736 B2 | 3/2005 | Sawatari et al. |
| 6,926,674 B2 | 8/2005 | Tenerz et al. |
| 6,938,474 B2 | 9/2005 | Melvangs |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway et al. |
| 7,060,038 B2 | 6/2006 | Letort et al. |
| 7,097,620 B2 | 8/2006 | Corl et al. |
| 7,112,170 B2 | 9/2006 | Schock et al. |
| 7,134,994 B2 | 11/2006 | Alpert et al. |
| 7,137,953 B2 | 11/2006 | Eigler et al. |
| 7,211,048 B1 | 5/2007 | Najafi et al. |
| 7,222,539 B2 | 5/2007 | Tulkki |
| 7,229,403 B2 | 6/2007 | Schock et al. |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway et al. |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson et al. |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson et al. |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,556,520 B2 | 10/2013 | Elenbaas et al. |

(56) References Cited

U.S. PATENT DOCUMENTS

| | | |
|---|---|---|
| 8,562,537 B2 | 10/2013 | Alpert et al. |
| 8,636,659 B2 | 1/2014 | Alpert et al. |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1* | 8/2004 | Reiser ............... A61B 18/24 606/7 |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan et al. |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith et al. |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Naghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1* | 10/2009 | Perkins ............... A61B 17/3478 606/159 |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0109104 A1 | 5/2010 | Tlensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn et al. |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0216481 A1 | 8/2013 | Rosenmeier |
| 2013/0303914 A1* | 11/2013 | Hiltner ............... A61B 8/12 600/449 |
| 2013/0324864 A1 | 12/2013 | Manstrom et al. |
| 2014/0024235 A1 | 1/2014 | Russell |
| 2014/0024950 A1 | 1/2014 | Hiltner et al. |

(56) References Cited

U.S. PATENT DOCUMENTS

| | | |
|---|---|---|
| 2014/0086461 A1 | 3/2014 | Yao et al. |
| 2014/0180140 A1 | 6/2014 | Alpert |
| 2014/0180141 A1 | 6/2014 | Millet |
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1* | 8/2015 | Ludoph ............ A61B 5/6852 600/487 |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0066802 A1 | 3/2016 | Keller |
| 2016/0106321 A1 | 4/2016 | Sharma et al. |

FOREIGN PATENT DOCUMENTS

| | | |
|---|---|---|
| EP | 1658808 | 8/1995 |
| EP | 1419796 | 5/2004 |
| EP | 1493381 | 1/2005 |
| EP | 1514512 | 3/2005 |
| EP | 1702641 A2 | 9/2006 |
| JP | 10-33488 A | 2/1998 |
| JP | 10-137199 A | 5/1998 |
| JP | 2004-194996 A | 7/2004 |
| JP | 2006-204378 A | 8/2006 |
| NL | 2009285 | 8/2012 |
| WO | WO97/00641 | 1/1997 |
| WO | WO99/58059 | 11/1999 |
| WO | WO03/022122 | 3/2003 |
| WO | WO2006/037082 | 4/2006 |
| WO | WO2006/117154 | 11/2006 |
| WO | WO2011/120565 | 10/2011 |
| WO | WO2011/161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

\* cited by examiner

CATHETER FOR PROVIDING VASCULAR PRESSURE MEASUREMENTS

FIELD OF THE INVENTION

The invention relates to a catheter for providing a vascular pressure measurement.

BACKGROUND OF THE INVENTION

The severity of a stenosis or lesion in a blood vessel may be assessed by obtaining proximal and distal pressure measurements relative to the given stenosis and using those measurements for calculating a value of the Fractional Flow Reserve (FFR). FFR is defined as the ratio of a distal pressure measurement ($P_d$) taken on the distal side of the stenosis and a proximal pressure measurement taken on the proximal side of the stenosis usually within the aorta ($P_a$). Conventionally, a sensor placed on the distal portion of a flexible interventional device, such as a guide wire, is utilized to obtain the distal pressure measurement $P_d$, while an external pressure transducer is fluidly connected via tubing to a guide catheter for obtaining the proximal or aortic pressure measurement $P_a$. Calculation of the FFR value provides a lesion specific index of functional severity of the stenosis in order to determine whether the blockage limits blood flow within the vessel to an extent that treatment is needed. An optimal or normal value of RR in a healthy vessel is 1.00, while values less than about 0.80 are generally deemed significant and in need of an interventional treatment. Common interventional treatment options include balloon angioplasty and/or stent implantation.

Blood flow through the coronary arteries is affected by fluctuations in the pressure arising proximally of the lesion, e.g., in the aorta, as well as fluctuations in pressure arising distally of the lesion, e.g., in the microcirculation. Accordingly, it is not possible to accurately assess the severity of a coronary lesion by simply measuring the pressure differential across the lesion because the pressure measurement taken on the distal side of the lesion is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These vasodilator agents reduce the dramatic fluctuation in resistance to obtain a relatively stable and minimal resistance value, Although various solutions have been proposed for providing the proximal and distal pressure measurements ($P_a$, $P_d$) for calculating an FFR value, there remains a need in the art for alternative devices and methods for obtaining pressure measurements suitable for use in calculating an FFR value for a given stenosis.

BRIEF SUMMARY OF THE INVENTION

Embodiments hereof are directed to a catheter for providing pressure measurements at a vascular lesion. The catheter includes an outer component having a side opening for providing transverse access to a lumen thereof and an inner component slidably disposed within the lumen. The inner component has a guidewire lumen with a proximal side port. When the inner component is longitudinally translated relative to the outer component, the side port of the inner component is accessible through the side opening of the outer tubular component for providing transverse access to a guidewire. A first pressure sensor is disposed proximate of a distal end of the outer component and a second pressure sensor is disposed proximate of a distal end of the inner component, such that relative longitudinal translation between the inner and outer components permits a distance between the first and second pressure sensors to be varied.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1AA is an enlarged sectional view of an alternate tip construction for the catheter of FIG. 1 in accordance with another embodiment.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used to measure the pressure gradient over heart valves and may also be used in any other body passageways where it is deemed useful. Furthermore, there is no intention to be bound by any expressed or implied theory presented in the preceding technical field, background, brief summary or the following detailed description.

Figure 1:
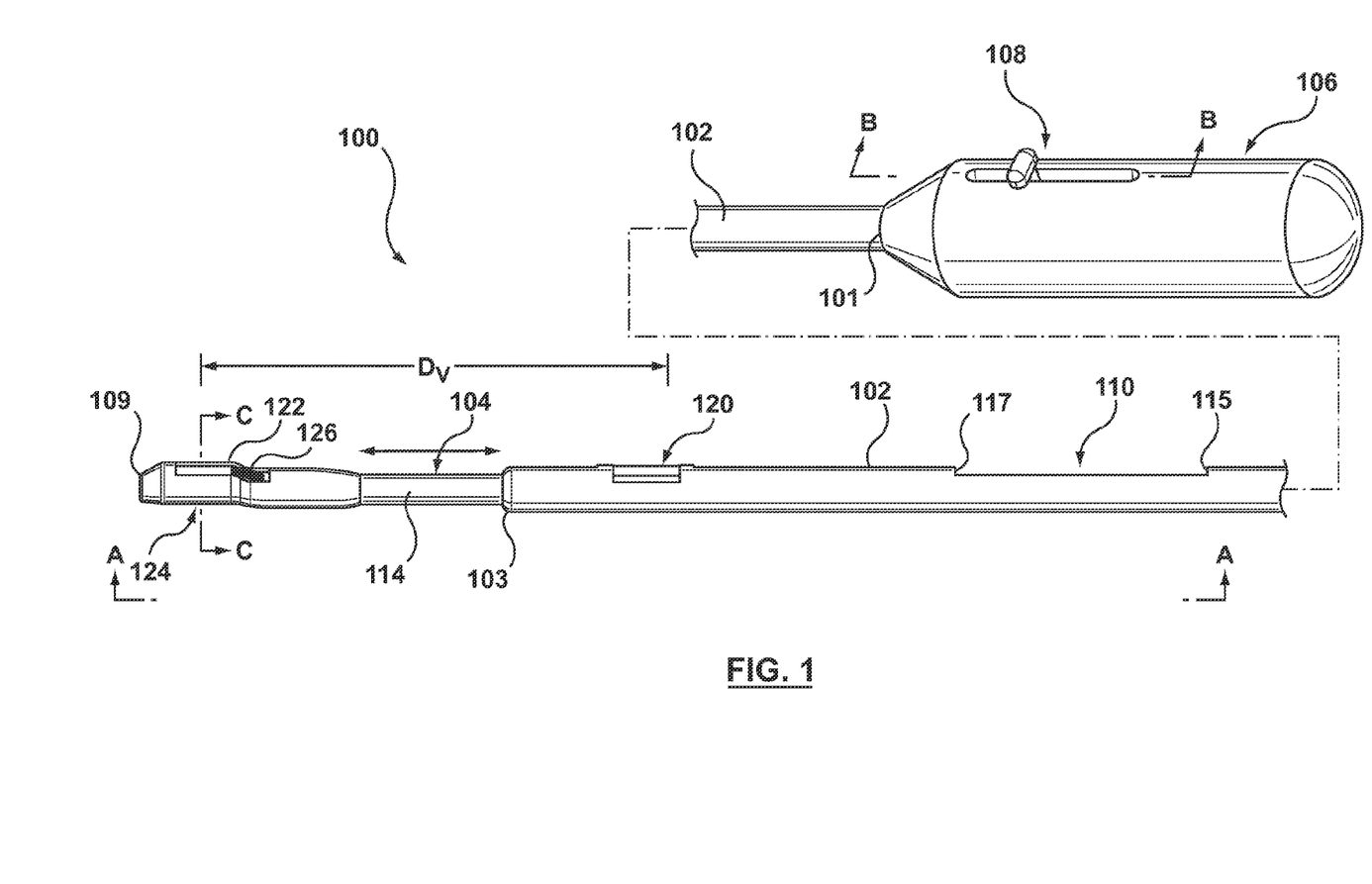
FIG. 1 is a perspective side view of a catheter in accordance with an embodiment hereof.
Figure 1A:
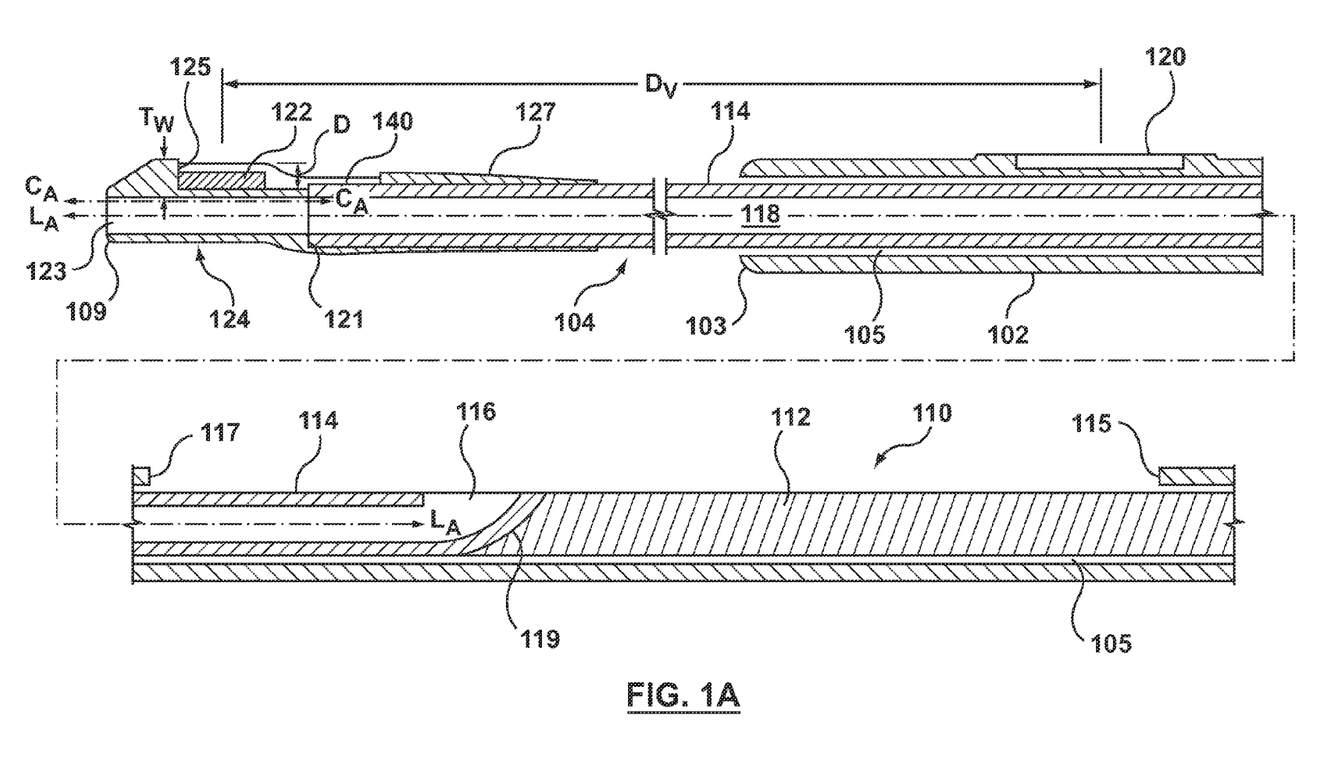
FIG. 1A is an enlarged sectional view of a distal portion of the catheter of FIG. 1 taken along line A-A thereof.
Figure 1B:
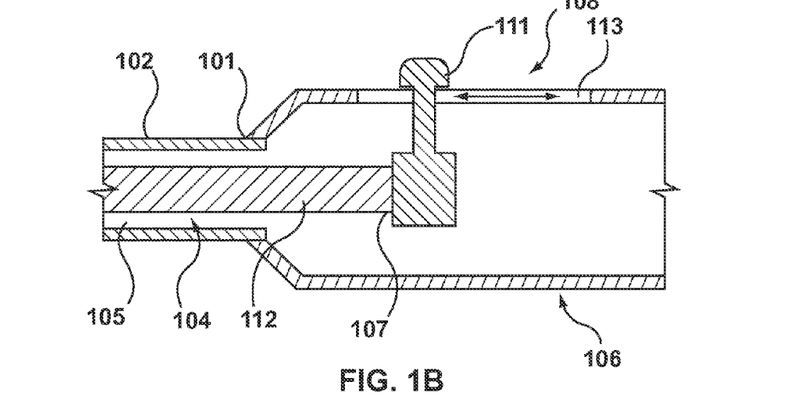
FIG. 1B is an enlarged sectional view of a proximal portion of the catheter of FIG. 1 taken along line B-B thereof.

FIG. 1 is a perspective side view of a catheter 100 for providing pressure measurements at a target site of a stenosis or lesion in accordance with an embodiment hereof. FIG. 1A is a sectional view of catheter 100 taken along line A-A of FIG. 1. FIG. 1B is a sectional view of catheter 100 taken along B-B of FIG. 1. Catheter 100 includes an elongate outer shaft or tubular component 102, an elongate inner shaft or component 104, and a handle component 106. A proximal end 101 of outer shaft 102 is attached to handle component 106 and a distal end 103 of outer shaft 102 has a first pressure sensor 120 attached proximate or adjacent thereto. In an embodiment, pressure sensor 120 is at least partially embedded within outer shaft 102 to reduce a profile thereof, which may be achieved by placing the sensor into a recess and applying an adhesive to hold it therein. An encapsulating material, such as silicone, may be used to insulate and protect the sensor, and may also be used to hold the sensor in place. Outer shaft 102 defines a lumen 105 from proximal end 101 to distal end 103 thereof and includes a side opening 110 for providing transverse access to lumen 105. Side opening 110 is a longitudinally extending slot that has a first or proximal end 115 and a second or distal end 117. In the embodiment shown in FIGS. 1 and 1A, pressure sensor 120 is disposed distal of side opening 110 and aligned therewith. In other embodiments, pressure sensor 120 may be disposed at another location about a circumference of outer shaft 102 that does not align with side opening 110 without departing from the scope hereof.

Inner shaft 104 slidably extends within lumen 105 of outer shaft 102. A proximal end 107 of inner shaft 104 is operably coupled to an actuation mechanism 108 of handle component 106. An atraumatic distal tip 124 forms a distal end 109 and a distal port 123 of inner shaft 104. Distal tip 124 has a second pressure sensor 122 attached thereto such that pressure sensor 122 is disposed proximate of or adjacent to distal end 109 of inner shaft 104. Inner shaft 104 includes an elongate proximal portion or segment 112 and a distal portion or segment 114. Proximal portion 112 is configured to have columnar strength for pushability and in accordance with embodiments hereof may be at least partially formed by a push wire or hypotube. Distal portion 114 is a polymeric tube extending from proximal portion 112 that is sized to have a minimal outer diameter for enabling inner shaft 104 to be disposed across a stenosis or lesion without undesirably disrupting the blood flow therethrough. A distal end 121 of distal portion 114 is secured to distal tip 124. A proximal end 119 of distal portion 114 is configured to form a side port or opening 116 of inner shaft 104. As shown in FIG. 1A, guidewire lumen 118 extends from side port 116 to distal port 123 of inner shaft 104 and as such is defined by distal portion 114 and distal tip 124. Catheter 100 is constructed to maintain alignment of side port 116 of inner shaft 104 with side opening 110 of outer shaft 102 to thereby permit transverse access for a guidewire to be slidably received through guidewire lumen 118. In another embodiment in accordance herewith, inner shaft 104 may be a polyimide tube with proximal portion 112 having a braided layer and/or an outer polymeric jacket for added stiffness and with distal portion 114 being formed to include a rapid exchange joint that defines side port 116. Alternatively a portion or the entire inner shaft 104 may be formed of polyether block amide (PEBAX), or another thermoplastic with or without a braided layer and/or by utilizing a hypotube.

Figure 1C:
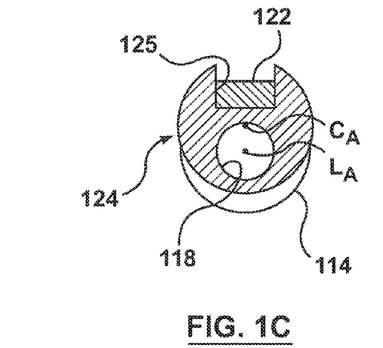
FIG. 1C is a sectional view of the catheter of FIG. 1 taken along line C-C thereof
Figure 1D:
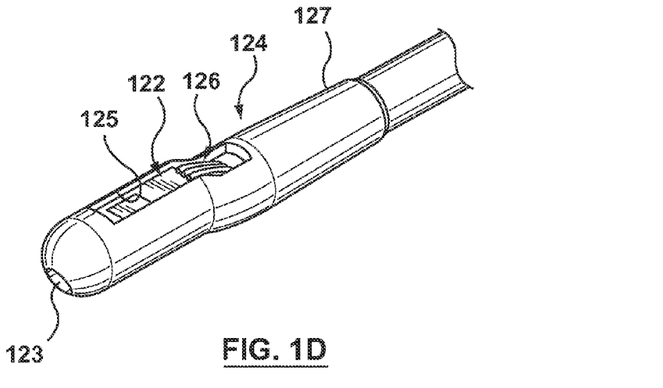
FIG. 1D is a perspective view of a distal tip of the catheter of FIG. 1.

In the embodiment shown in FIGS. 1, 1A, 1C and 1D, distal tip 124 is of a polymeric material and may be over-molded onto distal portion 114 or formed as a separate part and bonded thereto. As shown in FIGS. 1A and 1C, the portion of guidewire lumen 118 that is formed by distal tip 124 is off-center with respect to a central axis $C_A$ thereof. Pressure sensor 122 is housed in a sensor recess 125 that is formed within a thick-wall $T_W$ of distal tip 124 on an opposite side of the central axis $C_A$ from guidewire lumen 118. Sensor recess 125 of distal tip 124 is formed to have a depth D that permits pressure sensor 122 to be disposed within distal tip 124 below an outer surface 140 of distal portion 114 of inner shaft 104. Sensor recess 125 also proximally extends over distal end 121 of distal portion 114 to accommodate an external portion of the electrical connections 126 of pressure sensor 122, with the remainder of the electrical connections being embedded within and/or wrapped around inner shaft 104 as the electrical connections extend to handle component 106. Distal tip 124 includes a tapered proximal portion 127 that is sized to be slidably received within lumen 105 of outer shaft 102 when catheter 100 is in a delivery configuration, as described below with reference to FIG. 2A. The benefit of the distal tip construction described herein is that an overall reduced outer diameter can be achieved for catheter 100 and particularly inner shaft 104, as pressure sensor 122 may be disposed closer to a longitudinal axis $L_A$ of inner shaft 104, as shown in FIG. 1A, than it otherwise could be if the pressure sensor is mounted on outer surface 140 of distal portion 114, as shown in FIG. 1AA and described below.

More particularly in an alternate embodiment shown in FIG. 1AA, a distal tip 124A may be over-molded onto outer surface 140 of distal end 121 of distal portion 114 of inner shaft 104 such that distal tip 124A surrounds distal portion 114. In such an embodiment, distal portion 114 extends through the length of distal tip 124A such that guidewire lumen 118 and distal port 123 are formed by distal portion 114. Although the tip construction of FIG. 1AA may result in a larger overall outer diameter, as distal tip 124A is entirely disposed on inner shaft 104, the construction provides a more stable distal tip and a continuous guidewire lumen through distal portion 114 of inner shaft 104, which may improve tracking performance.

Figure 2A:
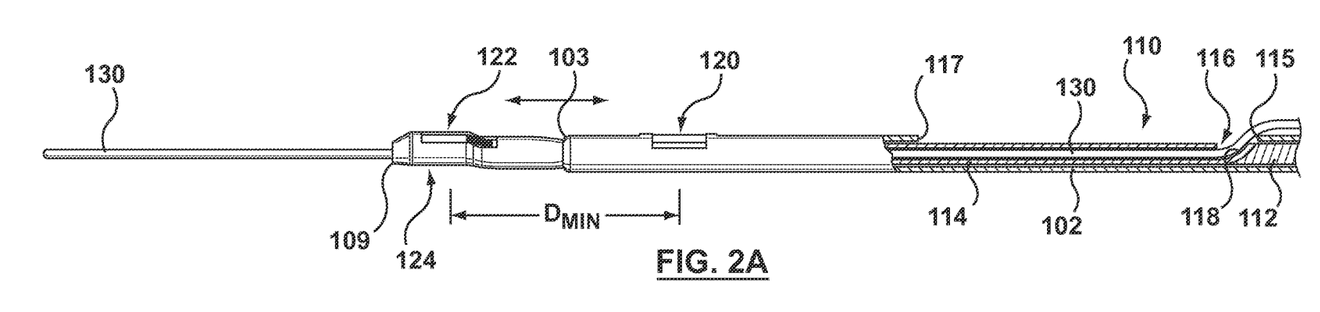
FIG. 2A is a side view in partial section of a distal portion of the catheter of FIG. 1 in a delivery configuration.
Figure 2B:
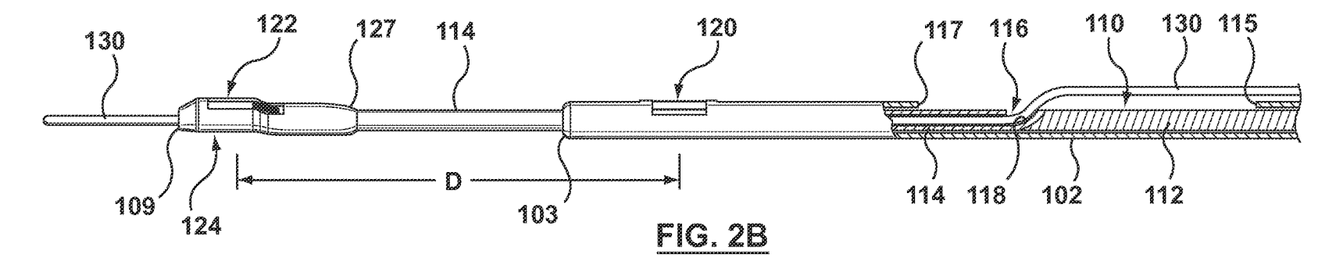
FIG. 2B is a side view in partial section of a distal portion of the catheter of FIG. 1 with first and second pressure sensors thereof spaced apart a distance D.
Figure 2C:
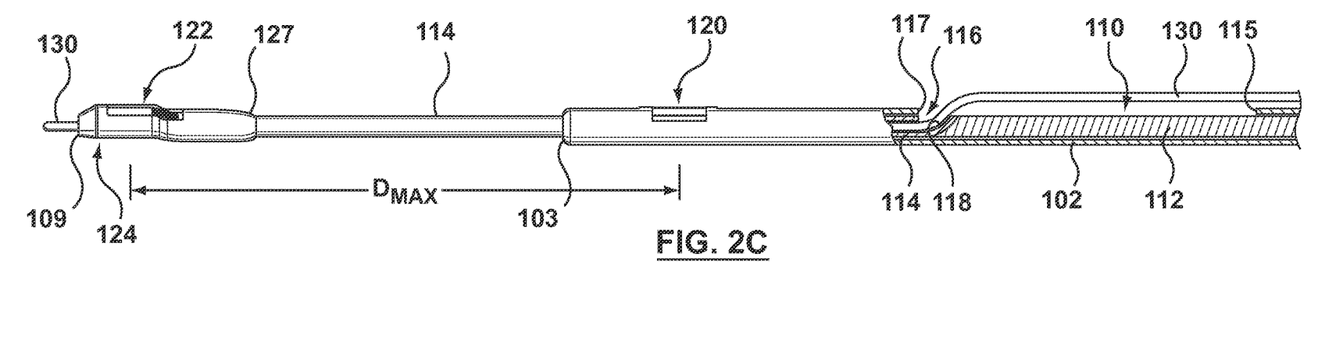
FIG. 2C is a side view in partial section of a distal portion of the catheter of FIG. 1 with first and second pressure sensors thereof spaced apart a distance $D_{MAX}$.

In the embodiment shown in FIGS. 1 and 1B, actuation mechanism 108 includes a slider 111 that slides within a corresponding slot 113 of handle component 106. When slider 111 is distally or proximally translated within slot 113, slider 111 correspondingly translates inner shaft 104 in a longitudinal direction relative to outer shaft 102 to thereby vary a distance $D_V$ between pressure sensor 122 at distal end 109 of inner shaft 104 and pressure sensor 120 at distal end 103 of outer shaft 102. During longitudinal translation of inner shaft 104 within lumen 105 of outer shaft 102, side port 116 of inner shaft 104 is correspondingly slidable between first and second opposing ends 115, 117 of side opening 110 to be accessible by a guidewire at all times. Accordingly, catheter 100 is a rapid-exchange catheter such that during a minimally invasive percutaneous interventional procedure only a relatively short distal segment of the catheter is tracked over a guidewire. With reference to FIGS. 2A-2C, for example, a guidewire 130 is shown extending through side opening 110, side port 116, and guidewire lumen 118 when catheter 100 is in various configurations. In FIG. 2A catheter 100 is shown tracked over a guidewire 130 in an initial or delivery configuration with tapered proximal portion 127 of distal tip 124 of inner shaft 104 being received within distal end 103 of outer shaft 102 and with sensors 120, 122 spaced apart a minimum distance "$D_{MIN}$." In the delivery configuration of FIG. 2A, side port 116 of inner shaft 104 is disposed adjacent to proximal end 115 of side opening 110 of outer shaft 102. In the configuration of catheter 100 shown in FIG. 2B, inner shaft 104 is shown longitudinally translated along guidewire 130 relative to outer shaft 102 to space apart sensors 120, 122 a distance "D," whereby side port 116 is centrally disposed between proximal and distal ends 115, 117 of side opening 110. In the configuration of catheter 100 shown in FIG. 2C, inner shaft 104 is shown longitudinally translated along guidewire 130 relative to outer shaft 102 to space apart sensors 120, 122 a maximum distance "$D_{MAX}$," whereby side port 116 is disposed adjacent to distal end 117 of side opening 110.

Figure 3:
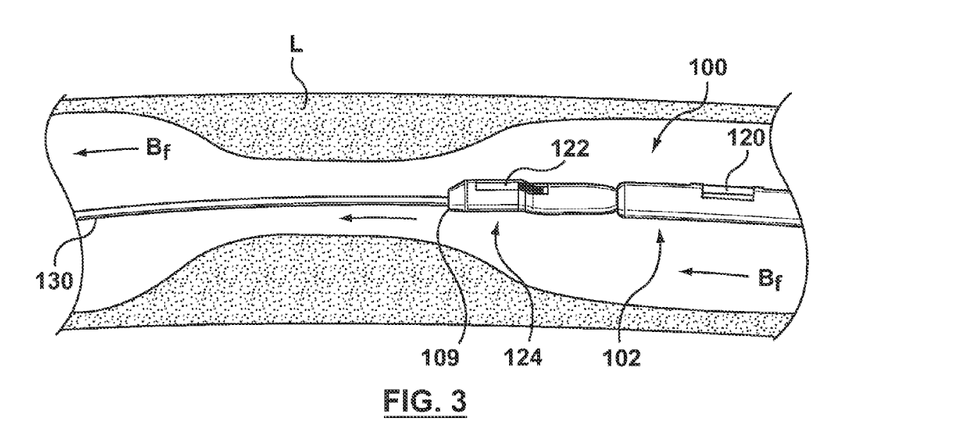
FIG. 3 depicts a distal portion of a catheter in accordance with embodiments hereof positioned adjacent a lesion in the vasculature.
Figure 4:
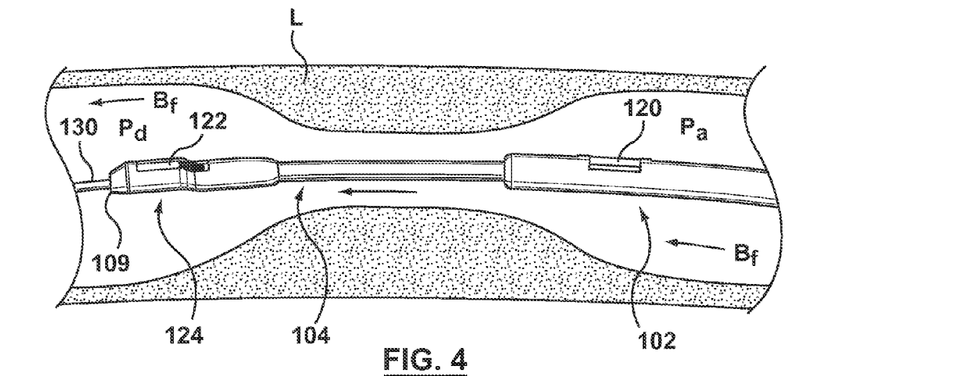
FIG. 4 depicts a distal portion of a catheter in accordance with embodiments hereof positioned across a lesion in the vasculature.

In a method in accordance herewith, a guide catheter (not shown) is tracked through the vasculature until a distal end thereof is disposed within the aorta proximal of an ostium of a branch vessel within which a lesion or stenosis of interest is located. With reference to FIG. 3 that shows blood flow $B_f$ through a portion of a vessel having a lesion L, guidewire 130 is advanced through the guide catheter to be disposed across the lesion L. Thereafter, catheter 100 in the delivery configuration shown in FIG. 2A is tracked over the indwelling guidewire 130 to a target site of the lesion L and positioned such that distal end 109 of inner shaft 104 is proximal of the lesion L. Slider 111 of actuation mechanism 108 is then slid distally within slot 113 of handle component 106 to distally advance inner shaft 104 relative to outer shaft 102 until distal tip 124 and pressure sensor 122 thereon are positioned distal of the lesion L, as shown in FIG. 4. Accordingly, pressure sensor 120 on outer shaft 102 remains proximal of the lesion L. In one embodiment, adenosine is administered either intracoronary at the site by bolus, or intravenously by continuous infusion for enhancing the accuracy of the pressure measurements ($P_a$, $P_d$) for an FFR value. A proximal pressure measurement ($P_a$) with pressure sensor 120 and distal pressure measurement ($P_d$) with pressure sensor 122 are then simultaneously taken to provide the FFR value, $P_d/P_a$, for the lesion. Catheter 100 may then be completely withdrawn from the patient or repositioned in vivo at another lesion and the process repeated.

Figure 5:
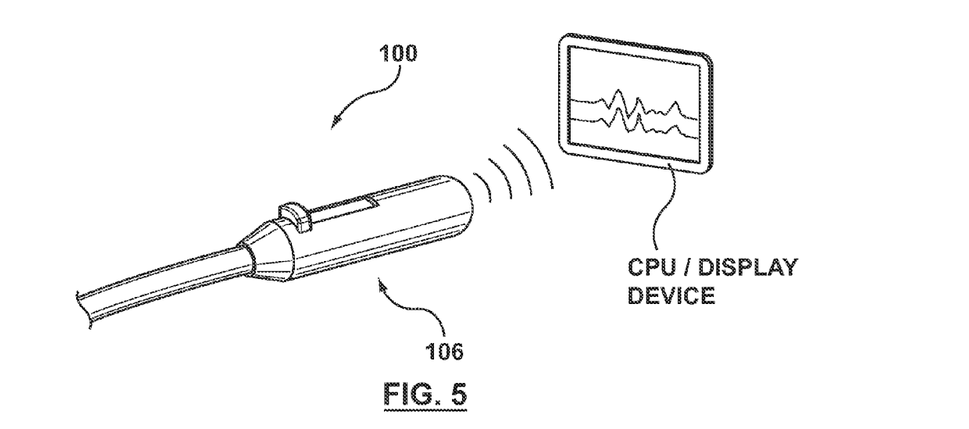
FIG. 5 is a depiction of a handle component of a catheter in accordance with embodiments hereof communicating with an external CPU/Display Device.

FIG. 5 depicts handle component 106 wirelessly communicating the pressure measurements ($P_a$, $P_d$) with a CPU having a display device. In an embodiment, the sensors 120, 122 may communicate the sensed pressures to an amplification and filtering device and an analog-to-digital converter (ADC) contained within handle component 106 that communicate with the external CPU and display device. In an alternate embodiment, the CPU may be contained in the handle component or be a separate component from the display device.

In embodiments hereof, an elongate shaft or tubular component and/or portions or layers thereof may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. In other embodiments of an elongate shaft or tubular component in accordance herewith, a proximal portion thereof may be a hypotube of a medical grade stainless steel with a distal portion thereof being formed from any of the polymeric materials listed above.

Electrical connections for the first and second pressure sensors, such as power leads, extend from the respective sensors to the handle component of the catheter. In other embodiments of an elongate shaft or tubular component in accordance herewith, the shaft or a portion thereof may be formed by a tubular polymeric inner liner overlaid with a power lead layer and a polymeric outer jacket. In one such embodiment, the power leads for the respective pressure sensors of the inner and outer shafts may be wrapped around the inner liner of the respective shaft for all or at least a portion of the shaft and secured in position by the polymeric outer jacket so as to be embedded within the shaft. In another such embodiment, the power leads for the respective pressure sensors of the inner and outer shafts may be straight for a section or for the entire length of the shaft and secured in position against the inner liner by the polymeric outer jacket so as to be embedded within the shaft.

Pressure-sensing catheters in accordance with embodiments hereof may be used for other than providing proximal and distal pressure measurements ($P_a$, $P_d$) for calculating an FFR value. For instance, pressure-sensing catheters in accordance with embodiments hereof may be used to provide an in vivo pressure measurement anywhere along the vasculature, or a particular lesion therein. As well, embodiments hereof may be used to provide in vivo pressure measurements, across a heart valve, venous valve or other valvular location within the body where it may be deemed useful.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter comprising:
   an outer tubular component having a side opening for providing transverse access to a lumen thereof and including a first pressure sensor disposed proximate of a distal end thereof; and
   an inner component having a guidewire lumen that extends between a side port and a distal port of the inner component, and including a second pressure sensor disposed proximate of a distal end thereof,
   wherein the inner component is configured to be longitudinally translatable within the lumen of the outer tubular component such that the side port of the inner component is slidable between a proximal end and a distal end of the side opening of the outer tubular component, and wherein longitudinal translation of the inner component relative to the outer tubular component permits a distance between the first pressure sensor and the second pressure sensor to be varied,
   wherein the distance between the first pressure sensor and the second pressure sensor includes a minimum distance wherein the side port of the inner component is disposed adjacent the proximal end of the side opening of the outer tubular component and a maximum distance wherein the side port of the inner component is disposed adjacent the distal end of the side opening of the outer tubular component.

2. The catheter of claim 1, wherein the second pressure sensor is disposed within a distal tip of the inner component.

3. The catheter of claim 2, wherein the catheter includes a delivery configuration for tracking through a vasculature to a treatment site and a measurement configuration for measuring pressures proximal and distal of a lesion at the treatment site, wherein in the delivery configuration, a tapered proximal portion of the distal tip is received within the distal end of the outer tubular component.

4. The catheter of claim 2, wherein the inner component includes a tubular distal portion attached to the distal tip and wherein the tubular distal portion and the distal tip define the guidewire lumen of the inner component.

5. The catheter of claim 4, wherein a portion of the guidewire lumen that extends within the distal tip is off-center with respect to a central axis of the distal tip.

6. The catheter of claim 2, wherein the second pressure sensor and at least a portion of electrical connections that extend therefrom are disposed within a sensor recess of the distal tip.

7. The catheter of claim 1, wherein a proximal end of the inner component is operably coupled to an actuation mechanism, the actuation mechanism being configured to longitudinally translate the inner component relative to the outer tubular component to thereby vary the distance between the first and second pressure sensors.

8. The catheter of claim 7, wherein the actuation mechanism is a slider that is slidable within a corresponding slot of a handle component.

9. The catheter of claim 7, wherein at least a proximal portion of the inner component is one of a push wire and a hypotube.

10. The catheter of claim 1, wherein the first pressure sensor is embedded within a wall of the outer tubular component to thereby reduce an overall profile of the catheter.

11. The catheter of claim 1, wherein alignment of the side port of the inner component with the side opening of the outer tubular component permits transverse access for a guidewire to be slidably received within the guidewire lumen.

12. A catheter comprising:
an outer shaft defining a lumen from a proximal end to a distal end thereof and having a side opening for providing transverse access to the lumen, the outer shaft having a first pressure sensor disposed thereon that is positioned distal of the side opening; and
an inner shaft that defines a guidewire lumen from a side port of the inner shaft to a distal port of the inner shaft, wherein the inner shaft is longitudinally translatable within the lumen of the outer shaft such that the side port of the inner shaft is accessible through the side opening of the outer shaft for slidably receiving a guidewire therethrough, and
wherein the inner shaft includes a distal tip having a second pressure sensor disposed thereon such that longitudinal translation of the inner shaft relative to the outer shaft permits a distance between the first pressure sensor and the second pressure sensor to be varied,
wherein the distance between the first pressure sensor and the second pressure sensor includes a minimum distance wherein the side port of the inner shaft is disposed adjacent a proximal end of the side opening of the outer shaft and a maximum distance wherein the side port of the inner shaft is disposed adjacent a distal end of the side opening of the outer shaft.

13. The catheter of claim 12, wherein the catheter includes a delivery configuration for tracking through a vasculature to a treatment site and a measurement configuration for measuring pressures proximal and distal of a lesion at the treatment site, wherein in the delivery configuration, a tapered proximal portion of the distal tip is received within the distal end of the outer shaft.

14. The catheter of claim 12, wherein the inner shaft includes a tubular distal portion attached to the distal tip, the tubular distal portion having an outer diameter sized to be slidably received within the lumen of the outer shaft and having a proximal end that defines the side port of the inner shaft.

15. The catheter of claim 14, wherein the tubular distal portion and the distal tip define the guidewire lumen of the inner shaft.

16. The catheter of claim 15, wherein a portion of the guidewire lumen that extends within the distal tip is off-center with respect to a central axis of the distal tip.

17. The catheter of claim 12, wherein the inner shaft further includes a proximal end operably coupled to an actuation mechanism, the actuation mechanism being configured to longitudinally translate the inner shaft relative to the outer shaft to thereby vary the distance between the first and second pressure sensors.

18. The catheter of claim 17, wherein the actuation mechanism is a slider that is slidable within a corresponding slot of a handle component.

19. The catheter of claim 17, wherein at least a proximal portion of the inner shaft is one of a push wire and a hypotube.

20. The catheter of claim 12, wherein the first pressure sensor is embedded within the outer shaft and the second pressure sensor is embedded within the distal tip of the inner shaft to thereby reduce an overall profile of the catheter.

* * * * *